United States Patent [19]
Brewster

[11] 4,264,209
[45] Apr. 28, 1981

[54] GAS DETECTOR

[75] Inventor: Arthur E. Brewster, Thaxted, England

[73] Assignee: ITT Industries, Inc., New York, N.Y.

[21] Appl. No.: 10,634

[22] Filed: Feb. 9, 1979

[30] Foreign Application Priority Data

Feb. 16, 1978 [GB] United Kingdom ............... 6163/78

[51] Int. Cl.³ ............................... G01N 21/25
[52] U.S. Cl. ................................. 356/414; 250/343; 350/315; 356/51; 356/416; 356/437
[58] Field of Search ............... 356/416, 418, 419, 51, 356/437–439, 414, 434; 250/339, 343; 350/315, 318

[56] References Cited

U.S. PATENT DOCUMENTS

| 3,319,071 | 5/1967 | Werth et al. | 250/339 |
| 3,694,086 | 9/1972 | May | 356/419 |
| 3,756,726 | 9/1973 | Astheimer | 356/434 |
| 3,853,407 | 12/1974 | Dewey, Jr. | 356/51 |

*Primary Examiner*—F. L. Evans
*Attorney, Agent, or Firm*—A. Donald Stolzy

[57] ABSTRACT

Apparatus for illuminating a gas or gas mixture and filtering the output thereof alternately with two filters. One filter has a passband at an absorption band of a gas to be detected. The other filter has a passband outside the absorption band.

1 Claim, 13 Drawing Figures

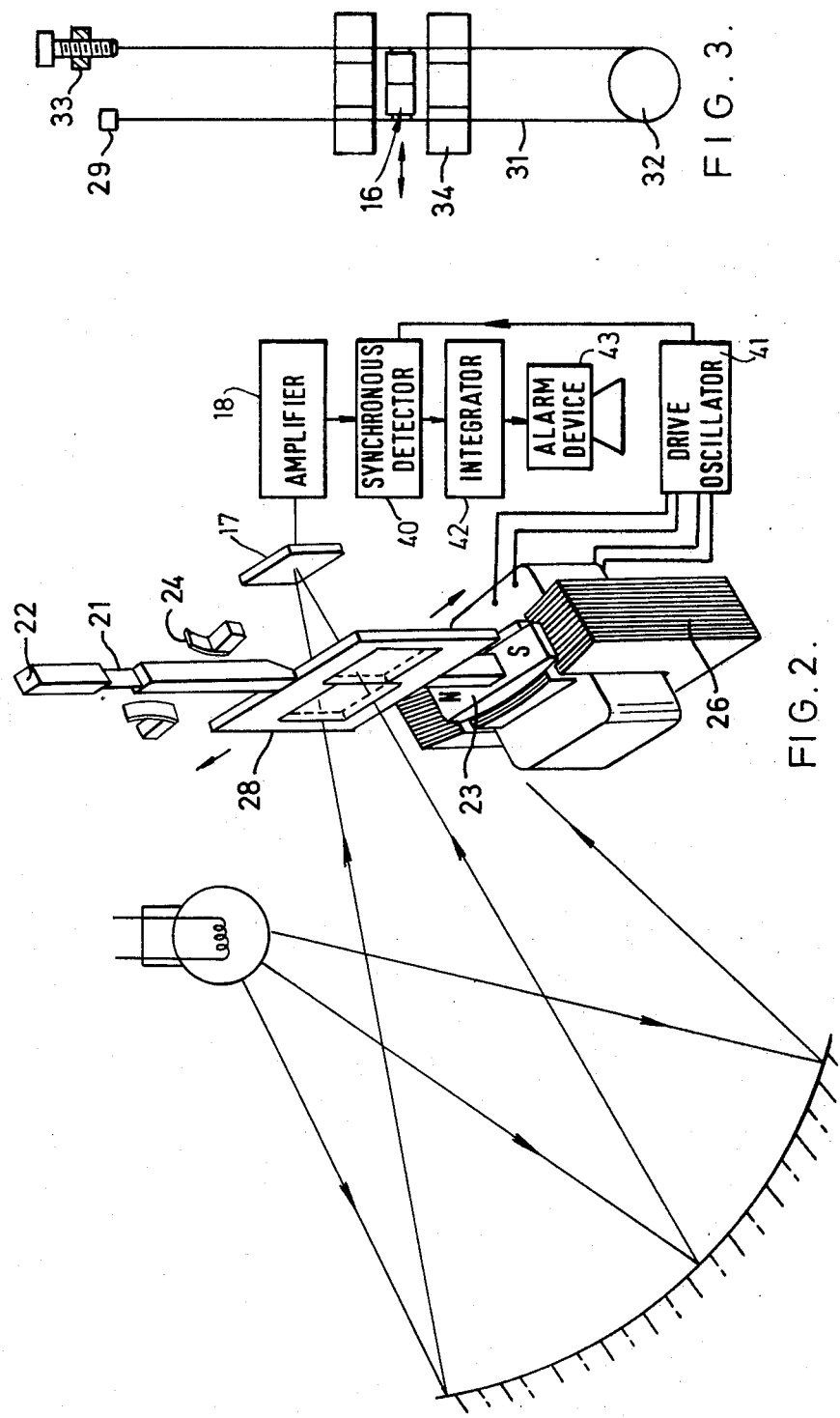

GAS DETECTOR

BACKGROUND OF THE INVENTION

This invention relates to arrangements for the detection of gases and/or vapors, and more particularly, to an arrangement for photometric analysis.

Recreational vehicles, mobile homes and small boats frequently use bottled gases, e.g., propane or butane, to provide heating and lighting facilities. A constant hazard with such a practice is the risk of leakage of the gas into a confined space. As such gases are heavier than air they tend to form a layer on the floor of the dwelling and can cause a fire or an explosion, or under some circumstances, can asphyxiate the occupants. Conventional detectors of the semiconductor type tend to be rather insensitive and are also non-specific. Thus, such a detector will often produce a response to tobacco smoke or even to exhaled breath.

PRIOR ART STATEMENT

In Snowman U.S. Pat. No. 3,588,496 issued June 28, 1971, cells 13 and 14 are alternatively exposed through chopper holes 24 and 23, respectively. An infrared detector 20 and magnetic detector 27 are both connected to a synchronous detector 21, the output of which is indicated at 22. The output of the synchronous detector 21 is proportional to the concentration of the gas to be measured.

SUMMARY OF THE INVENTION

According to one aspect of the invention there is provided a gas detector arrangement, including a light source, a light detector so arranged as to receive light from the source, an optical filter having a passband corresponding to an absorption band of the gas, and means for placing the filter in and out of the light path between the source and detector thereby causing the detector to produce an oscillatory signal the amplitude of which corresponds to the concentration of the gas.

According to another aspect of the invention there is provided a gas detector arrangement adapted to respond to the presence of a predetermined gas, the arrangement including a broad band light source, a receiver arranged so as to receive light from the source, a first optical filter having a passband corresponding to an absorption band of the gas, a second optical filter having a passband in a region of the spectrum adjacent to that of the absorption band, and oscillatory means for placing the filters alternately in the light path between the source and the detectors thereby causing the detector to produce an oscillatory signal the amplitude of which corresponds to the concentration of the gas in the light path.

The term "light" as used herein is hereby defined for use herein and in the claims to follow as to include the infrared, the visible and the ultra-violet regions of the spectrum.

BRIEF DESCRIPTION OF THE DRAWINGS

In the accompanying drawings which illustrate exemplary embodiments of the present invention:

FIGS. 2 and 3 are schematic diagrams of alternatives for use with the arrangement of FIG. 1;

DESCRIPTION OF THE PREFERRED EMBODIMENT

Figure 1:
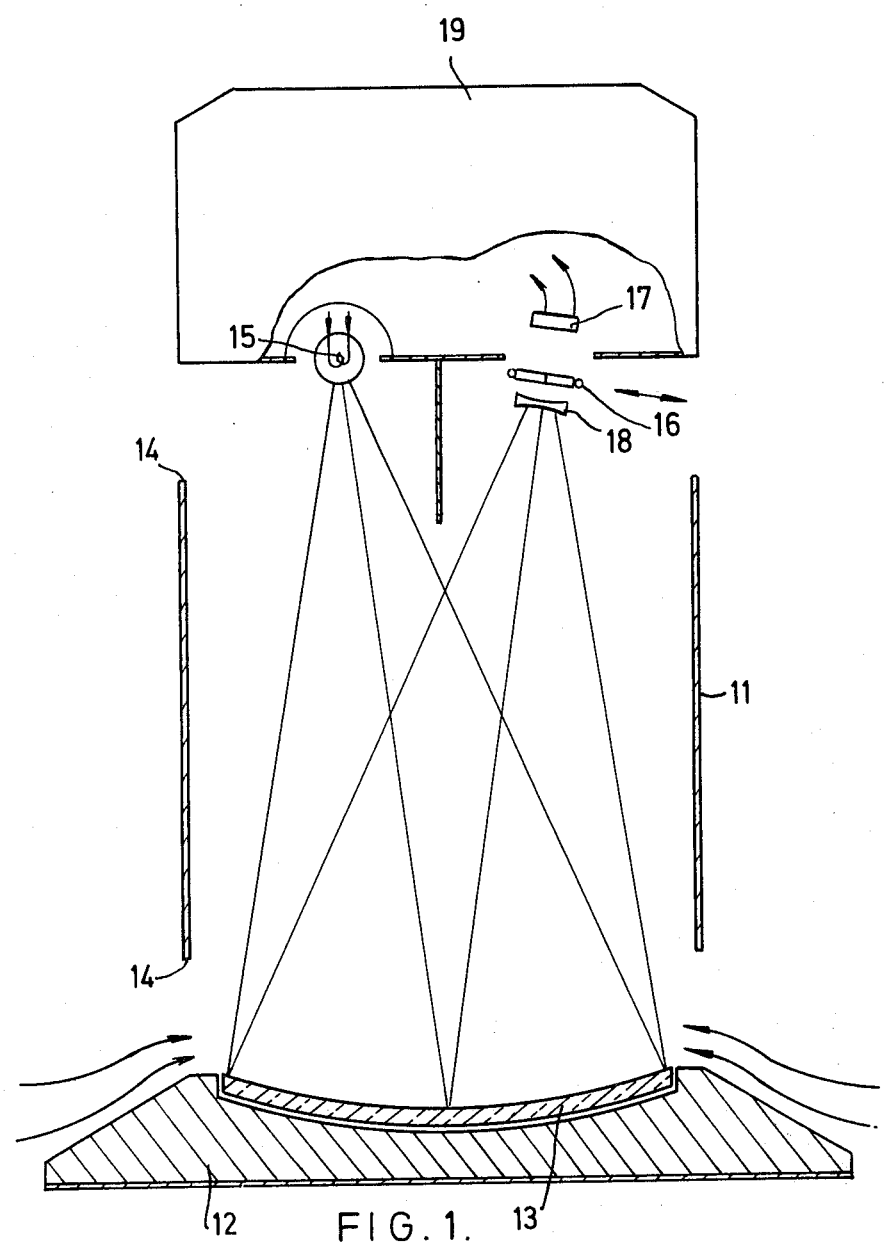
FIG. 1 is a schematic diagram of a gas detector constructed in accordance with the present invention.

Referring to FIG. 1, a gas detector arrangement constructed in accordance with the present invention is mounted within a housing 11 provided with a relatively heavy base portion 12, the central region of which is machined to form spherical mirror 13. The housing 11 has openings 14 to allow the passage of gas therethrough and, in use, would normally be placed on the floor of the compartment in which an inflammable gas is used.

A light source 15 is placed near the center of curvature of the spherical mirror 13, slightly displaced from the mirror axis. The resultant image is thereby similarly displaced to a position convenient for locating a filter chopper arrangement 16 and a photodetector 17. The volume of space between the mirror and the other optical components, which is open to the atmosphere, serves as the region in which light absorption takes place. The light from the source 15 traverses this region twice in its path to the photodetector 17. A collimator 18 may be provided to focus the light on detector 17. The upper portion 19 of the housing contains a battery, a detector amplifier and an alarm device.

It should be noted that, as the gas detector arrangement is normally operated at infrared wavelengths, a rear-silvered glass mirror cannot be used because the glass would not transmit the light at such wavelengths. Since the required accuracy of the reflecting surface is a function of the working wavelength, mirrors for use in the infrared may be of significantly lower quality than would be required in the visible light region. Thus, the mirror may be a simple lathe-turned spherical recess in the base of the instrument, after-treatment being limited to a few moments polishing with a hand-held cloth and metal polish. The quality of the mirror need be no better than sufficient to return the major part of the incident light; in fact, since the objective is to achieve uniform illumination of the photodetector 17, it is preferable that any irregularities in the emission from the light source 15 should not be too precisely imaged upon the photodetector. In some applications the mirror may comprise a plastic molding flashed with a suitably reflective coating.

The chopper 16 comprises a pair of filters disposed adjacent to each other on a mechanically-resonant member so that the oscillatory movement will interpose first one filter and then the other into the light path. An electronic oscillator serves to maintain the resonant member and its filters in continuous vibration. One filter (F1 in FIG. 4), subsequently to be referred to as the absorption filter, has a construction so as to pass light occupying a restricted bandwidth centered on the chosen optical wavelength at which light is absorbed by the gas to be detected. The other filter F2 is constructed to have a passband straddling a reference wavelength at which the gas does not absorb light and which is not disturbed by the presence of other gases of no immediate concern. Oscillation of the filters from FIG. 4a to FIG. 4c and back, samples first one wavelength, then the other, and then the one, repetitively. The photodetector 17 (FIG. 1) gives an output determined by the amount of light traversing the path at any instant, so that any unbalance between the light transmission at the two wavelengths generates an A.C. waveform having an amplitude proportional to the amount of unbalance, and a frequency and phase coincident with that of the filter chopper 16.

In the absence of the gas to be detected, the light transmission at the two wavelengths will, for example, be equal. The A.C. component of the detector output may then be zero. Balancing means may be added so as to enhance this condition. The presence of the gas to be detected attenuates the light within the absorption spectra but not as the reference wavelength. This creates an unbalance signal which may be amplified and made to trigger an alarm.

The arrangement described herein is intended to detect propane or butane (both heavier-than-air gases). In consequence, the optical axis has been disposed vertically so as to place the mirror 13 (FIG. 1) close to the floor, and the base of the instrument so shaped as to encourage the easy ingress of gas from any direction.

In FIG. 2 one arrangement is shown for providing oscillatory motion of the filters F1 and F2. The filters F1 and F2 are mounted on a carrier 28 at one end of a spring strip 21, the other end of which is secured to a mount 22. The other end of the carrier 28 carries a bar magnet 23, the outwardly facing surface of which is ground to a radius of curvature corresponding to or slightly less than the distance of an electromagnet 26 from the mount 22. Vibration of the spring 21 is restricted by limit stop springs 24 against which the carrier 28 abuts at the extremities of its vibratory excursions. The arrangement is driven by electromagnet 26 which has three poles. Electromagnet 26 is arranged adjacent to the bar magnet 23. An alternating current is supplied to electromagnet 26 at a frequency equal to the resonant frequency resulting from the combination of the supporting spring 21, limit stop springs 24, the total mass of the system, the magnet 23 and the electromagnet 26.

The 3-pole actuating electromagnet 26 may advantageously be provided by a 1:1 audio transformer with its core cut away in an appropriate arc. The electromagnet 26 is so arranged that an air gap of about 1 mm exists between the pole tips and the armature 23. The supporting spring 21 is comparatively light, providing little restoring force, so that energy stored in the armature 23 as it accelerates across the pole tips is expended mainly in depressing the limit stop springs 24. Upon recovery, the limit stop springs 24 return the energy to the armature 23 to launch it back across the pole tips, assisted by the small drive current. The Q of the mechanically resonant system is such that only about 20 milliwatts are required from the electronic driver to maintain continuous oscillation. The mechanically resonant system is closely coupled to the electronic oscillator and serves as the frequency-determining element. There are thus no synchronization problems.

The absorption filter F1 may be an interference filter of 2% bandwidth centered on 3.35 microns—the preferred absorption wavelength for propane. The reference wavelength is determined by a similar filter F2 centered, e.g., on 3.95 microns. The selection of the absorption and reference wavelengths has an effect upon the choice of the remaining components of the optical system. Quartz cuts off at about 4.7 microns, enabling the use of a conventional quartz-halogen lamp.

Some results are achieved by using a ceramic pyroelectric photodetector. This is not wavelength-dependent. A lead selenide photodetector is preferred. With it a slightly higher sensitivity at significantly lower cost can be obtained.

In FIG. 2, photodetector 17 is shown, the output of which is connected to an amplifier 18. The output of amplifier 18 is synchronously detected in a detector 40 having an input connected from a drive oscillator 41.

The output of detector 40 is impressed upon an integrator 42, the output of which, in turn, is impressed upon a conventional alarm device 43.

FIG. 3 shows an alternative filter vibrator arrangement. In this arrangement a loop of high-tensile wire 31, e.g., steel, is rigidly attached at one end at 29. It then passes around a freely-rotatable pulley 32 before returning to another point of attachment adjacent to the first, at which point a suitable tensioning means 33 is provided so as to enable adjustment of the resonant frequency of the system. The arrangement thus provides a pair of parallel wires of equal length and, by the intervention of the pulley, equal tension, thereby endowing them both with the same resonant frequency. The two points of attachment are electrically insulated from each other, and serve also as input terminals for a suitable driving waveform. The pulley 32 is also insulated so as to avoid short-circuiting the drive waveform. The filter chopper assembly 16 is attached so as to bridge the pair of wires, as shown, at their centers where the amplitude of vibration will be at a maximum. The bridge, also, is insulated so as not to short-circuit the drive waveform.

The resonant wires are embraced by a magnet system 34 which generates lines of magnetic force disposed at right angles to the direction of the wires. Polarities are so arranged that when drive current is passed around the loop, the forces on the two wires are such as to displace them both in the same direction as well as assembly 16. The two-wire support provides accurate control of the filter angle and position while allowing freedom for the desired sideways movement.

In the absence of a gas to be detected it is preferable that the amount of light passing through the filters F1 and F2 should be equalized. One method of effecting balancing is achieved by adopting the filter configuration shown in FIGS. 4a to 4i, in which the light path is taken to be emerging normal to the paper surface.

Figure 4A:
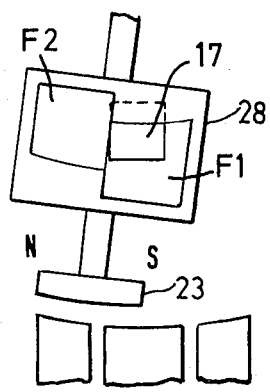
FIGS. 4a–4i show the method filter tuning.
Figure 4B:
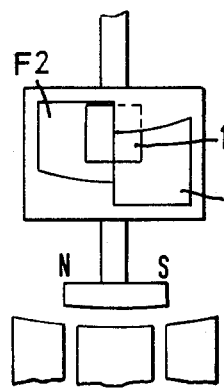
Figure 4C:
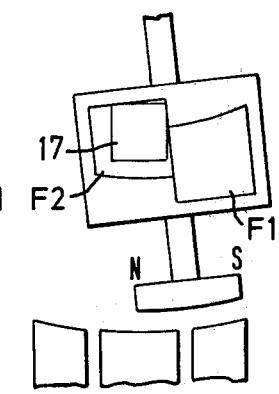
Figure 4D:
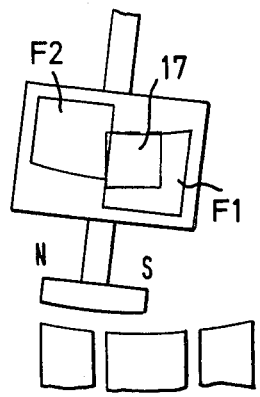
Figure 4E:
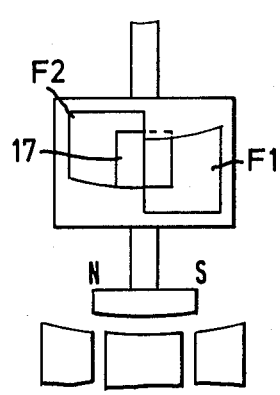
Figure 4F:
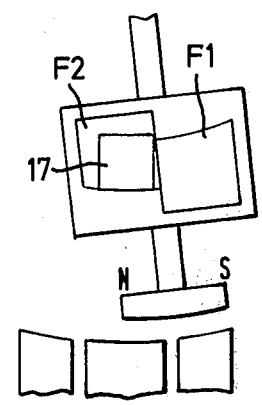
Figure 4G:
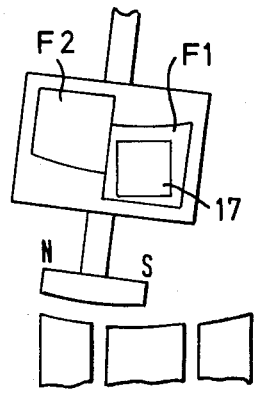
Figure 4H:
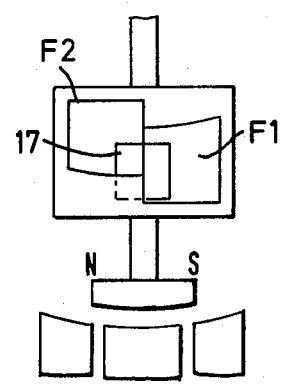
Figure 4I:
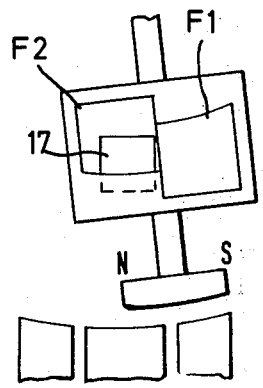

In the normal chopping cycle, the filters F1 and F2 will swing from side to side in relation to the optical aperture, exposing first the reference filter F2, (FIGS. 4a, 4d and 4g) and then the absorption filter F1 (FIGS. 4c, 4f and 4i). Between these extremes (FIGS. 4b, 4e and 4h) the carrier or chopper 28 assumes a transition mode in which one filter progressively takes over from the other, passing through a neutral position where the optical aperture is momentarily shared equally between the two filters. This sequence will be seen to prevail in FIGS. 4d to 4f, where the optical aperture is fully exposed essentially throughout the entire chopping cycle.

A balancing adjustment can be achieved by moving the whole vibrator unit, including the drive electromagnet upwards or downwards in relation to the detector 17.

If the vibrator unit is displaced downward the aperture may be partially obscured during the passage of filter F2 as at FIGS. 4a and 4b. If the unit is displaced upward, as in FIGS. 4g to 4i the converse will occur. By displacement of the vibrator unit, this masking effect may be made to compensate for static differences in the light transmitted at the two wavelengths, the setting-up adjustment being made such as to achieve minimum photodetector output under no-gas conditions.

Figure 5:
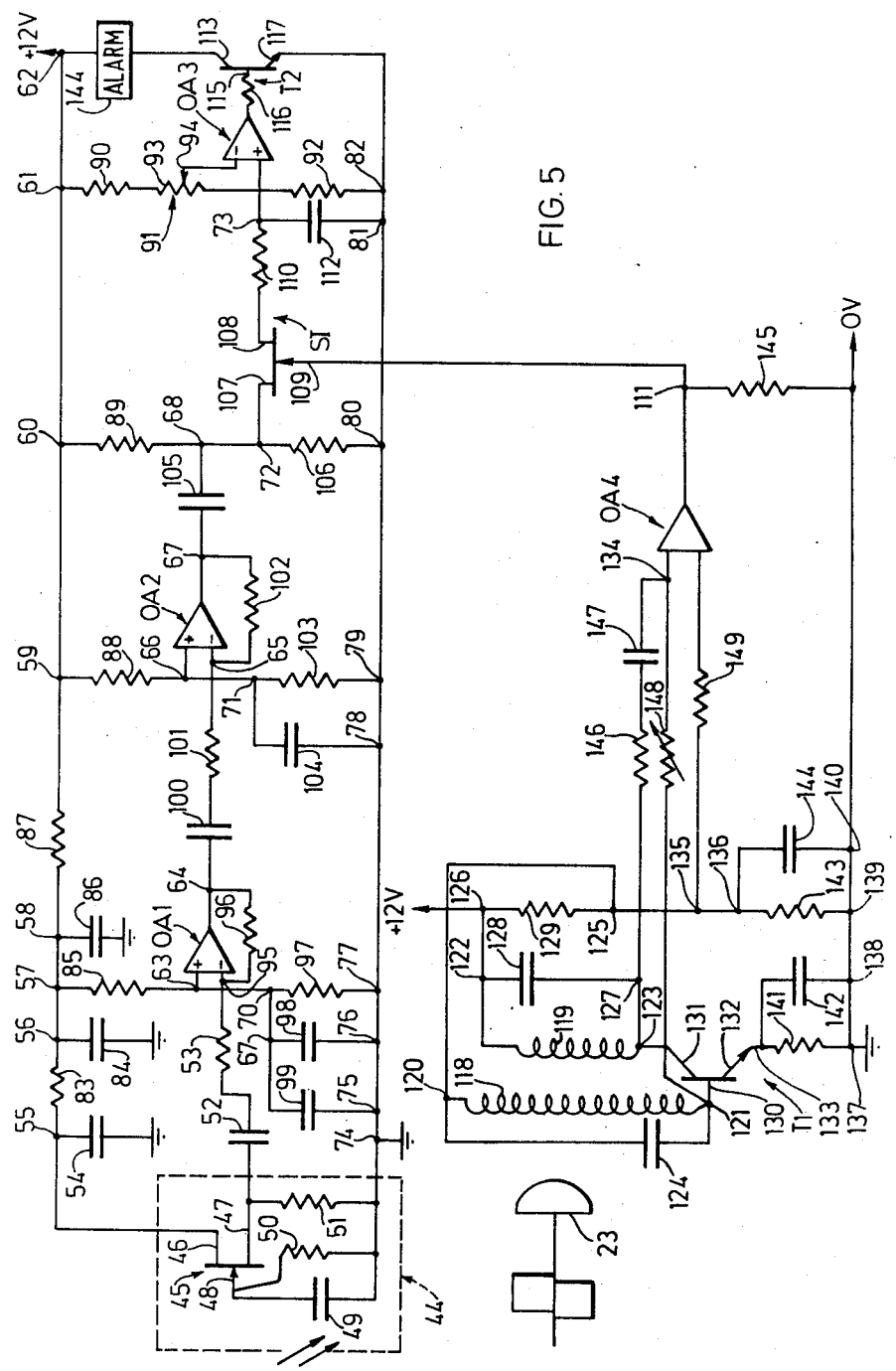
FIG. 5 is a schematic diagram of a suitable detector amplifier circuit for use in the arrangement of FIG. 1.

The drive circuit for the vibrator, shown in FIG. 5, is a simple tuned-base, tuned-collector transistor oscillator. Feedback is effected via 1:1 audio transformer adapted to serve also as the drive electromagnet in the manner described earlier. In operation, the magnetically polarized vibrator armature generates an EMF which reacts on the circuit so as to lock its oscillation rigidly to the mechanical resonance. This ensures that temperature or supply voltage changes cannot cause the electronic oscillator to lose synchronism with the mechanical vibrator. The coupling is so close that, if the vibrator is physically restrained, the circuit also stops oscillating. Nevertheless the oscillation is self-starting at switch-on. The mechanically resonant mode of operation ensures that power losses are minimal.

The photodetector is followed by a two-stage ac-coupled amplifier.

Synchronous rectification of the unbalanced waveform is performed by the switch S1. This may be provided by one section of a COS/MOS quad bilateral switch, but may also be a suitable FET device. The switching square wave is derived from the vibrator drive oscillator by an adjustable phase-shifting network followed by a squaring amplifier. The phase adjustment is provided to permit the substitution of photodetectors, because whereas the lead selenide cell produces an output proportional to illumination, the ceramic pyroelectric cell has an output proportional to the rate of change of illumination, that is, in quadrature with the phase of vibration. In some applications this adjustment could be eliminated, and the phase preset by initial choice of component values.

The output from a synchronous switch S1 is fed to a simple RC integrator and thence to the non-inverting input of the threshold-detecting and squaring amplifier. This input is normally held at a dc potential of about +6 volts, via S1, by the pair of resistors immediately preceding S1. Similarly, the inverting input is raised in potential by the resistor chain incorporating the "adjust sensitivity threshold" potentiometer. On setting up, this potentiometer is adjusted to place the inverting input of an amplifier OA3 slightly positive of its non-inverting input. In this state, the output of amplifier OA3 lies close to the negative supply rail and a transistor T2 is cut off.

In the presence of the gas to be detected, a resulting unbalance waveform appears at the output of the photodetector amplifier, the "on" phase of the switch S1 being made such that successive positive-going half-cycles of the waveform pass so as to raise the state of charge of the integrator capacitor. In the manner familiar to the art, the potential on this capacitor will rise to the mean value of the successive samples taken over the integration time, thus truly reproducing the unbalanced amplitude despite the presence of random photodetector noise or other non-synchronous disturbances. Should the unbalanced amplitude become sufficient to carry the non-inverting input of amplifier OA3 positive of its inverting input, amplifier OA3 output will switch immediately to the positive supply potential, turning-on transistor T2 and activating the alarm device.

In FIG. 5, a conventional photodetector is illustrated at 44. Photodetector 44 may be an infrared detector model PPC522 of the pyroelectric type, if desired.

Detector 44 includes a field effect transistor (FET) 45 having a drain 46, a source 47 and a gate 48.

Gate 48 is connected to ground through a capacitor 49. A resistor 50 is connected in parallel with capacitor 49.

A resistor 51 is connected from source 47 to ground. A capacitor 52 and a resistor 53 are connected in that order from source 47 to the inverting input of an amplifier OA1.

A capacitor 54 is connected from drain 46 to ground.

Junctions are provided at 55, 56, 57, 58, 59, 60, 61, 62, 63, 64, 65, 66, 67, 68, 69, 70, 71, 72, 73, 74, 75, 76, 77, 78, 79, 80, 81 and 82.

A resistor 83 is connected between junctions 55 and 56. A capacitor 84 is connected from junction 56 to ground. Junctions 56, 57 and 58 are connected together. A resistor 85 is connected between junctions 57 and 63. A capacitor 86 is connected from junction 58 to ground. A resistor 87 is connected between junctions 58 and 59. A resistor 88 is connected between junctions 59 and 66. A resistor 89 is connected between junctions 60 and 68. A resistor 90, a potentiometer 91 and a resistor 92 are connected in that order from junction 61 to junction 82.

Potentiometer 91 has a winding 93 and a wiper 94 connected to the inverting input of an amplifier OA3.

Junctions 63, 69 and 70 are connected together.

Resistor 53 is connected to a junction 95 which, in turn, is connected to the inverting input of amplifier OA1. A resistor 96 is connected between junctions 64 and 95.

A resistor 97 and capacitors 98 and 99 are connected in parallel from junction 70 to ground.

A capacitor 100 and a resistor 101 are connected in that order from junction 64 to junction 65.

Junction 64 is connected from the output of amplifier OA1. Junction 65 is connected to the inverting input of an amplifier OA2. A resistor 102 is connected between junctions 65 and 67. An output of amplifier OA2 is connected to junction 67. Junctions 66 and 71 are connected together. A resistor 103 is connected in parallel with a capacitor 104. Resistor 103 and capacitor 104 are connected from junction 71 to ground.

A capacitor 105 is connected between junctions 67 and 68. Junctions 68 and 72 are connected together. A resistor 106 is connected between junctions 72 and 80. FET S1 is provided to act as a switch. The FET S1 has a drain 107, a source 108, and a gate 109 connected respectively to junction 72, a resistor 110 and a junction 111. Resistor 110 is connected from source 108 to junction 73. A capacitor 112 is connected between junctions 73 and 81. Junction 73 is connected to the non-inverting input of amplifier OA3. Transistor T2 has a collector 113 connected to junction 62 through alarm 114. Junction 62 is connected to +12 volts.

Transistor T2 has a base 115 which is connected from the output of amplifier OA3 through a resistor 116. Transistor T2 has an emitter 117 which is connected to junction 82.

Also shown in FIG. 5, for connection with junction 111, is a transformer including windings 118 and 119 connected between junctions 120, 121 and 122 and 123, respectively. A capacitor 124 is connected between junctions 120 and 121. Junction 120 is connected to a junction 125.

Junction 122 is connected to a junction 126. Junction 126 is maintained at a potential of +12 volts. A junction is provided at 127. A capacitor 128 is connected between junctions 122 and 127. Junctions 123 and 127 are connected together. A resistor 129 is connected between junctions 125 and 126.

A transistor T1 is provided having a base 130 connected from junction 121, a collector 131 connected to junction 123 and an emitter 132 connected to a junction 133.

Junctions 134, 135, 136, 137, 138, 139 and 140 are also provided.

A resistor 141 is connected between junctions 133 and 137. A capacitor 142 is connected between junctions 133 and 138. A resistor 143 is connected between junctions 136 and 139. A capacitor 144 is connected between junctions 136 and 140. Junctions 125, 135 and 136 are connected together.

An amplifier is provided at OA4 having an output connected to junction 111. A resistor 145 is connected from junction 111 to 0 volts. Junctions 137, 138, 139 and 140 are all connected to 0 volts and to ground. A resistor 146 and a capacitor 147 are connected in that order from junction 127 and junction 134. Junction 134 is connected to one input of amplifier OA4. A variable resistor 148 is connected from junction 121 to junction 134.

A fixed resistor 149 is connected with junction 135 to another input to amplifier OA4.

As explained previously, the input to FET S1 over gate 109 synchronously detects the optical signal received by photodetector 44.

Values of components of FIG. 5 may be as follows:

|  |  |
| --- | --- |
| Capacitor 54 | 100 microfarads |
| Capacitor 84 | 100 microfarads |
| Capacitor 86 | 1 nanofarad |
| Capacitor 98 | 1 nanofarad |
| Capacitor 99 | 100 microfarads |
| Capacitor 100 | 4.7 microfarads |
| Capacitor 104 | 1 nanofarad |
| Capacitor 105 | 4.7 microfarads |
| Capacitor 112 | 10 microfarads |
| Capacitor 124 | 100 microfarads |
| Capacitor 128 | 300 microfarads |
| Capacitor 142 | 1000 microfarads |
| Capacitor 144 | 1000 microfarads |
| Capacitor 147 | 0.1 microfarad |
| FET S1 | CD 4016 |
| Photodetector 44 | Pyroelectric infrared detector PPC522 |
| Potentiometer 91 | 100,000 ohms |
| Resistor 83 | 2,200 ohms |
| Resistor 85 | 1.8 megohms |
| Resistor 87 | 330 ohms |
| Resistor 88 | 1.8 megohms |
| Resistor 89 | 100,000 ohms |
| Resistor 90 | 47,000 ohms |
| Resistor 92 | 47,000 ohms |
| Resistor 96 | 5.6 megohms |
| Resistor 97 | 1.8 megohms |
| Resistor 101 | 56,000 ohms |
| Resistor 102 | 5.6 meg |
| Resistor 103 | 1.8 megohms |
| Resistor 106 | 100,000 ohms |
| Resistor 116 | 10,000 ohms |

|  |  |
| --- | --- |
| -continued | |
| Resistor 129 | 1,600 ohms |
| Resistor 141 | 270 ohms |
| Resistor 143 | 820 ohms |
| Resistor 145 | 100,000 ohms |
| Resistor 146 | 100,000 ohms |
| Resistor 148 | 470,000 ohms |
| Resistor 149 | 27,000 ohms |
| Transistor T1 | 2N3053 |
| Transistor T2 | 2N3053 |

Synchronous detector 40 (FIG. 2) is entirely conventional as are detector 17, amplifier 18, integrator 42, alarm 43 and oscillator 41 shown in FIG. 2

What is claimed is:

1. A system for producing an indication of the concentration of a gas of interest, comprising:
a support and a light source fixed relative to said support;
a light-sensing detector fixed relative to said support, said light source and said light-sensing detector being positioned at opposite ends of a light path in which said gas mixture can be present; a filter movable transversely into and out of said light path to illuminate said gas periodically by two different light spectra, said light-sensing detector being thereby illuminated in accordance with the concentration of said gas of interest, the transmission wavelength of said filter being so related to the absorption spectra of said gas of interest that the output signal of said light-sensing detector is a first alternating signal of an amplitude which is a function of said gas concentration; drive means for moving said filter through said light path periodically; and a synchronous detector connected to the output of said light-sensing detector and to said drive means to detect the output of said light-sensing detector in synchronism with operation of said drive means, said drive means comprising a pendulum and a leaf spring, said leaf spring suspending said pendulum from said support, said filter being mounted on said pendulum, a permanent magnet fixed to the bottom of said pendulum and having opposite ends poled in the direction of motion of said pendulum, a U-shaped ferromagnetic core fixed relative to said support below said permanent magnet and having at least two legs positioned adjacent to respective ones of the said opposite ends of said permanent magnet, said drive means further including an inductive winding around said core and source means for energizing said winding with a second alternating signal to cause said magnet ends to be attracted alternately to said respective core legs and to cause said pendulum to swing back and forth; and in which said system also comprises an indicator and said synchronous detector being connected to receive said first and second alternating signals and to impress an amplitude demodulated signal on said indicator.

* * * * *